United States Patent [19]

Ksoll et al.

[11] Patent Number: 5,430,186

[45] Date of Patent: Jul. 4, 1995

[54] PREPARATION OF CARBOXYLIC CHLORIDES

[75] Inventors: Peter Ksoll, Bonn; Wolfgang Reuther, Heidelberg; Roland Ettl, Hassloch, all of Germany

[73] Assignee: BASF Aktiengesellschaft, Ludwigshafen, Germany

[21] Appl. No.: 274,696

[22] Filed: Jul. 14, 1994

[30] Foreign Application Priority Data

Jul. 22, 1993 [DE] Germany ............... 43 24 605.2

[51] Int. Cl.⁶ ............... C07C 51/58; C07C 51/02
[52] U.S. Cl. ............... 562/857; 562/856
[58] Field of Search ............... 562/857, 856

[56] References Cited

U.S. PATENT DOCUMENTS 3,184,506  5/1965  Parker et al. ............... 562/857
5,166,427  11/1992  Hohmann et al. ............... 562/857

Primary Examiner—José G. Dees
Assistant Examiner—Dwayne C. Jones
Attorney, Agent, or Firm—Keil & Weinkauf

[57] ABSTRACT

A process for the continuous manufacture of carboxylic chlorides (I) of the general formula R-COCl, in which R stands for a C-organic radical containing from 1 to 30 C atoms, by the reaction of a carboxylic acid (II) with a reaction product (III) of phosgene (IV) and an N,N-substituted formamide (V), in which compounds II and III are passed in parallel flow upwardly into a zone, filled with compound III, in a reactor (1), the reaction mixture is allowed to rise in predominantly laminar flow, such that phase separation occurs to give a top I-phase and a bottom phase III' mainly comprising compound III and formamide formed and compound I is removed from the top phase and also portions of the bottom phase III' are removed at the rate at which they are formed.

2 Claims, 2 Drawing Sheets

PREPARATION OF CARBOXYLIC CHLORIDES

FIELD OF THE INVENTION

The present invention relates to an improved process for the continuous preparation of carboxylic chlorides (I) of the general formula R-COCl in which R stands for a C-organic radical containing from 1 to 30 C atoms, by the reaction of a carboxylic acid R-COOH (II) with a reaction product (III) of phosgene (IV) and an N,N-substituted formamide (V).

DESCRIPTION OF THE PRIOR ART

Carboxylic chlorides are reactive and industrially significant starting products for a large number of carboxylic acid derivatives such as esters and amides. The manufacture of carboxylic chlorides from carboxylic acids and phosgene takes place in accordance with the following general equation:

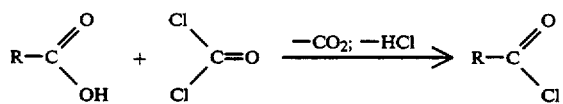

As a general rule, this reaction is carried out using a phosgene carrier, and N,N-substituted formamides have proven to be particularly suitable, as is generally known. These formamides form with the phosgene so-called Vilsmeyer compounds

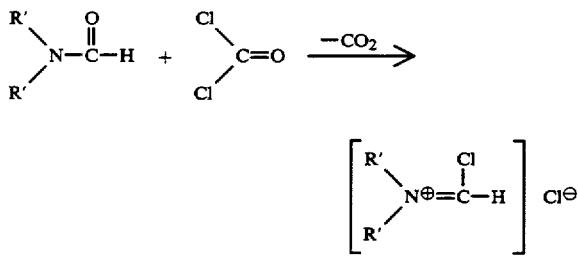

which act as the actual chlorinating agents with re-formation of the formamides:

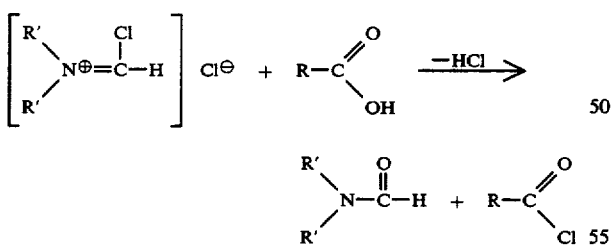

Since the formamides re-form, they are effective even when present in small amounts and are therefore referred to somewhat inaccurately as catalysts.

EP-A 475,137 specifically discloses that it is possible to feed carboxylic acid and phosgene into a stationary phase comprising the Vilsmeyer compound ("catalyst adduct") and to cause reaction thereof. The catalysts used are carbonamides, for example, preferably N-alkylformamide. The choice of catalyst system influences the course of the phosgenation of a carboxylic acid to the carboxylic chloride as well as further processing of the batch. In the process described in EP-A 475,137 an exhaust gas occurs however, which primarily consists of carbon dioxide and hydrogen chloride and which also contains a percentage of phosgene (p. 4, lines 43–44). Since the recovery of the hydrogen chloride is frequently uneconomical, the exhaust gas is neutralized with an aqueous alkaline solution, for example, a solution of calcium hydroxide or sodium hydroxide, to form the corresponding chlorides, which can then be easily disposed of. If larger amounts of carbon dioxide are present in the exhaust gas however, the carbonates are also formed, as a result of which an unnecessary increase in the consumption of neutralizing agent is caused.

SUMMARY OF THE INVENTION

It is thus an object of the present invention to overcome this drawback and to provide a process for the continuous preparation of carboxylic chlorides from carboxylic acid and phosgene in a manner which is, in all, more economical and simpler to carry out than hitherto.

Accordingly, we have found a process for the continuous preparation of carboxylic chlorides (I) of the general formula R-COCl, in which R stands for a C-organic radical containing from 1 to 30 C atoms, by the reaction of a carboxylic acid (II) with a reaction product (III) of phosgene (IV) and an N,N-substituted formamide (V), wherein compounds II and III are passed in parallel flow upwardly into a zone, filled with compound III, in a reactor (1), the reaction mixture is allowed to rise in predominantly laminar flow, such that phase separation occurs to give a top I-phase and a bottom phase III' mainly comprising compound III and formamide formed and compound I is removed from the top phase and also portions of the bottom phase III' are removed at the rate at which they are formed.

The substituent R has preferably the following meanings:

a $C_1$–$C_{30}$ alkyl group and especially a $C_8$–$C_{22}$ alkyl group such as 2-ethylhexyl or octadecyl a $C_2$–$C_{30}$ alkenyl group and especially a $C_8$–$C_{22}$ alkenyl group such as decenyl or octadecenyl a $C_2$–$C_{30}$ alkynyl group and especially a $C_8$–$C_{22}$ alkynyl group such as decynyl or octadecynyl a $C_3$–$C_8$ cycloalkyl group and especially a $C_5$–$C_8$ cycloalkyl group such as cyclopentyl or cyclohexyl, a $C_4$–$C_8$ cycloalkenyl group and especially a $C_5$–$C_6$ cycloalkenyl group such as cyclopentenyl or cyclohexenyl, a $C_7$–$C_{12}$ aralkyl group such as benzyl or 2-phenylethyl, an aryl group such as phenyl, naphth-1-yl, or naphth-2-yl.

These radicals may in turn carry inert substituents, for example, halogens such as fluorine, chlorine or bromine; nitro, cyano, $C_1$–$C_4$ alkoxy, $C_1$–$C_4$ acyl, $C_1$–$C_4$ acyloxy, and $C_1$–$C_4$ oxycarbonyl.

Figure 1:
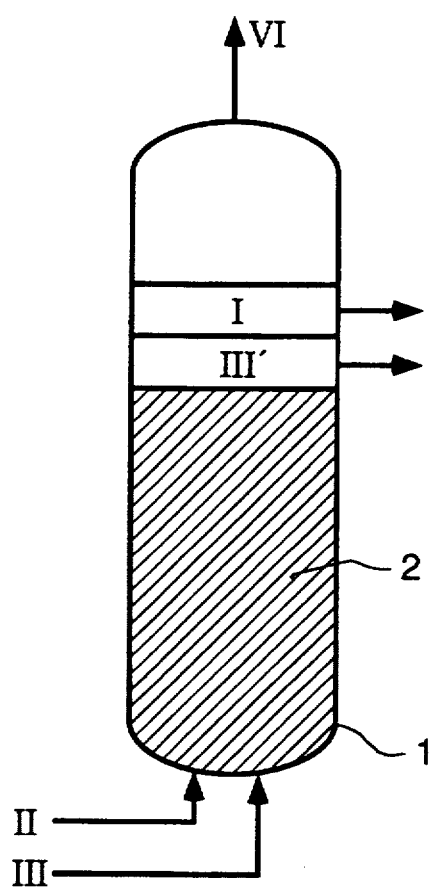
FIG. 1 is a flow diagram of a first embodiment illustrating the flow pattern of the reactor.

The process of the invention is described in greater detail below with reference to FIG. 1.

Carboxylic acid (II) and reaction product (III) are fed in parallel flow upwardly through a reactor (1) which contains in a reaction zone (2) a reaction product (III) of phosgene and an N,N-substituted formamide (V), prepared from phosgene and the formamide preferably immediately beforehand in separate apparatus. In the reaction the carboxylic chloride (I) is formed, and hydrogen chloride (VI) is liberated concurrently and the amount of chlorine in the compound (III) drops due to conversion to formamide (V) and thus a phase (III') is formed, which consists mainly of compound (III) and the formamide (V) formed.

The resulting components (I) and (III') collect above the reaction zone, where phase separation takes place due to differences in density. The carboxylic chloride (I) produced in a high degree of purity and the phase (III') are separated as liquid sidestreams and the hydrogen chloride (VI) liberated during the reaction is removed as overheads.

The addition of compounds (II) and (III) takes place in the reactor (1) at the rate at which compounds (I) and (III') are removed. To facilitate phase separation the rate of flow of the carboxylic acid (II) and reaction product (III) is adjusted such that virtually laminar flow is established.

The process is carried out predominantly at temperatures ranging from 20° to 140° C. and preferably from 30° to 70° C. and under standard pressure. Reduced pressure may be advantageous in order to facilitate separation of the cracked gases, and elevated pressure of, for example, up to 5 bar may be advantageous in the case of readily volatile components of the reaction mixture.

Suitable reactors are all those in which the reaction takes place without any appreciably backmixing, on the principle of a tubular reactor, that is, for example, vertical tubular reactors or spiral tubes which are immediately upstream of the phase-separating means. Brief intermixing of the reactants (II) and (III) can take place before they join the laminar flow of material in the reaction zone.

An excess of product (III) over the carboxylic acid (II) is advantageously used in the process although it is possible to use equimolar amounts. The off-gas of the reaction contains no substantial residue of phosgene, the concentration of which is usually between about 0.001 and 0.1 vol %.

The ratio of the height of the reactor to its diameter is in a range of from 5:1 to 200:1 and very preferably from 10:1 to 50:1.

Figure 2:
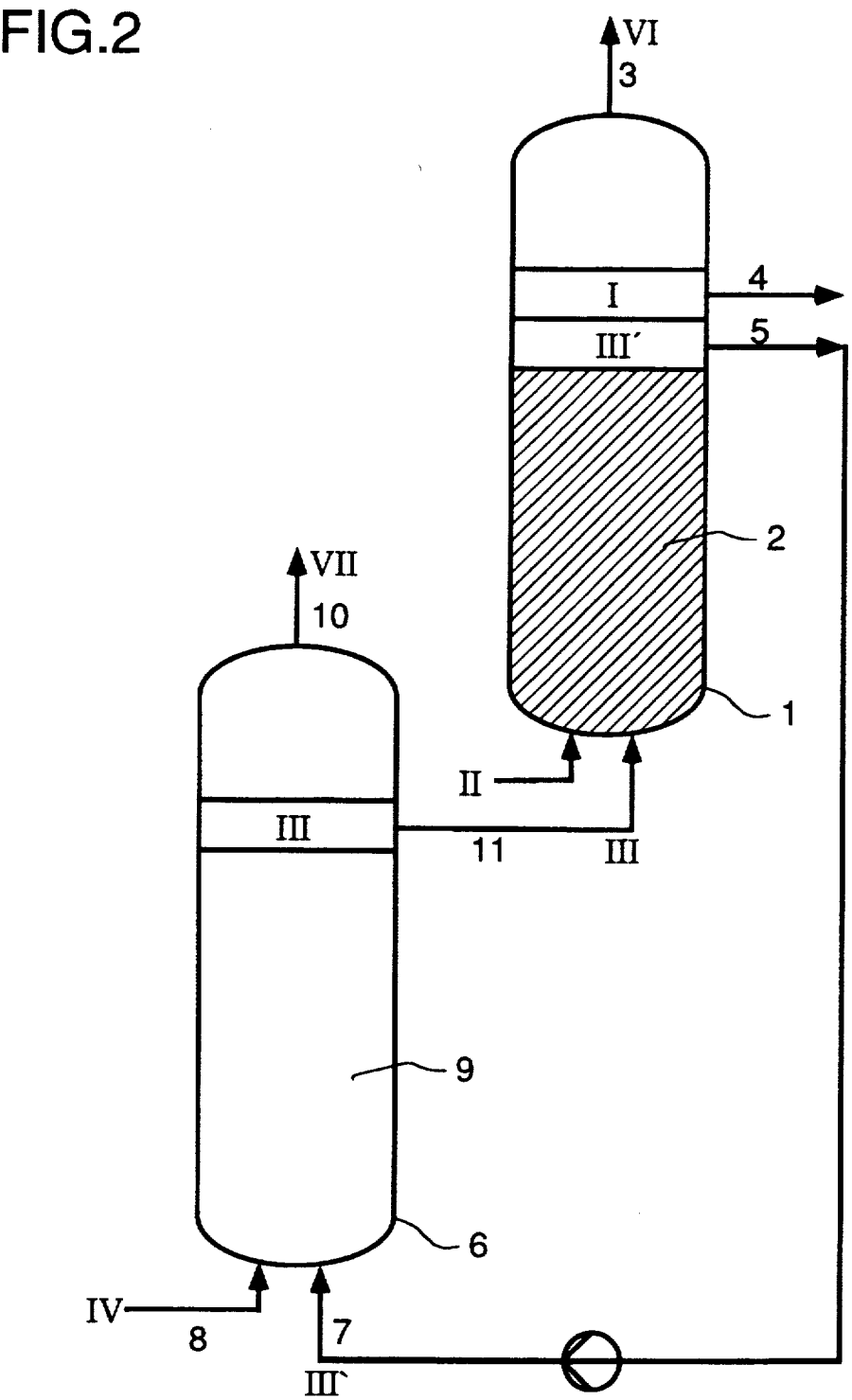
FIG. 2 is a flow diagram of a particularly preferred embodiment illustrating the flow pattern of the reactor.

A particularly preferred embodiment of the process of the invention including the preparation of the reaction product (III) is described in greater detail with reference to FIG. 2. On the lines of the process illustrated in FIG. 1, the formation of the carboxylic chloride (I) from the carboxylic acid (II) and the reaction product (III) takes place in the reaction zone (2) of the reactor (1), the liberated hydrogen chloride (VI) being removed at the top of the reactor via conduit (3). The carboxylic chloride (I) formed is removed via line (4).

The reaction product (III') is fed via line (5) to the bottom of a second reactor (6) via the inlet (7). Phosgene (IV) is fed to bottom of the reactor (6) via line (8). The reaction of the phosgene (IV) with the formamide (V) takes place in the reaction zone (9) of the reactor (6), and the reaction product (III) forms again with liberation of carbon dioxide (VII) which is removed from the reactor (6) via line (10). The reaction product (III) obtained is recycled to the reactor (1) via conduit (11).

To improve separation of the products carboxylic chloride (I) and reaction product (III') formed in the reactor (1), these materials can be together fed to another separating vessel, in which the individual components are isolated to a high degree of purity.

By means of conductivity indicators which measure by inductance, for example, the content of Vilsmeyer compound can be determined. A concentration of from about 50 to 80% is particularly preferred.

The circulation between the two reactors is caused by gas formation for one part but is also due to the reduction in density of the resultant carboxylic chloride. It can be assisted by pumps as required.

Substantially equimolar amounts of carboxylic acid (II) and phosgene (IV) are advantageously used in the process.

As necessary, an inert solvent can be added to the reaction mixture such as, for example, saturated aliphatic hydrocarbons, ethers, acetonitrile, benzene, toluene or cyclohexane. This is advantageous, for example, when use is made of solid acids or to improve phase separation.

Particularly suitable N,N-dialkylformamides are compounds having a total of up to 12 C atoms in the alkyl radicals, which can be the same or different or can alternatively together form a 5-membered to 7-membered ring.

The process of the invention provides a simple and economical way of continuously preparing carboxylic chlorides showing a high degree of purity. The exhaust gases hydrogen chloride (VI) and carbon dioxide (VII) produced during formation of the carboxylic chlorides occur separately and can be disposed of separately.

EXAMPLE

Preparation of Stearic Chloride

In a laboratory reactor having a height of 160 cm and a diameter of 10 cm there was placed a catalyst solution consisting of a reaction product of diethylformamide and phosgene. The percentage of activated Vilsmeyer compound in the catalyst solution was ca 75 wt %. Stearic acid were then added, each at the rate of 3 mol/h, at approximately 60° C.

The stearic chloride separated as the phase of lower specific gravity at the top of the reactor and was withdrawn. The isolated product contained 99.7 wt % of carboxylic acid chloride; the concentration of unconverted carboxylic acid was less than 0.1 wt %. The product was clear and had an iodine color value of 5.

We claim:

1. A process for the continuous preparation of carboxylic chlorides (I) of the general formula R-COCl, in which R stands for a C-organic radical containing from 1 to 30 C atoms, by the reaction of a carboxylic acid (II) with a reaction product (III) of phosgene (IV) and an N,N-substituted formamide (V), wherein compounds II and III are passed in parallel flow upwardly into a zone, filled with compound III, in a reactor (1), the reaction mixture is allowed to rise in predominantly laminar flow, such that phase separation occurs to give a top I-phase and a bottom phase III' mainly comprising compound III and formamide formed and compound I is removed from the top phase and also portions of the bottom phase III' are removed at the rate at which they are formed.

2. A process as claimed in claim 1, wherein the phase (III') formed in the reactor (1) is fed together with phosgene (IV) to a second reactor (6) in parallel flow, and the reaction product (III) obtained is recycled to the reactor (1).

* * * * *